United States Patent
Konno et al.

(10) Patent No.: US 11,219,368 B2
(45) Date of Patent: Jan. 11, 2022

(54) MOBILE DEVICE, SENSOR, PHYSIOLOGICAL INFORMATION MANAGEMENT METHOD, AND COMPUTER READABLE MEDIUM STORING PHYSIOLOGICAL INFORMATION PROCESSING PROGRAM

(71) Applicant: NIHON KOHDEN CORPORATION, Tokyo (JP)

(72) Inventors: Norihito Konno, Tokorozawa (JP); Fumiyuki Matsumura, Tokorozawa (JP); Hirohiko Ikeya, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 156 days.

(21) Appl. No.: 16/220,715

(22) Filed: Dec. 14, 2018

(65) Prior Publication Data
US 2019/0191997 A1 Jun. 27, 2019

(30) Foreign Application Priority Data
Dec. 26, 2017 (JP) .............................. JP2017-249706

(51) Int. Cl.
*A61B 5/00* (2006.01)
*H04W 4/38* (2018.01)
*A61B 5/0205* (2006.01)

(52) U.S. Cl.
CPC .......... *A61B 5/0022* (2013.01); *A61B 5/0024* (2013.01); *A61B 5/742* (2013.01);
(Continued)

(58) Field of Classification Search
CPC ...... H04W 4/38; A61B 5/0022; A61B 5/0024; A61B 5/742; A61B 5/0205; A61B 2562/08
See application file for complete search history.

(56) References Cited

U.S. PATENT DOCUMENTS

| 2005/0171444 A1 | 8/2005 | Ono et al. |
| 2005/0206218 A1* | 9/2005 | Clifford .................... B60B 7/20 |
| | | 301/37.25 |

(Continued)

FOREIGN PATENT DOCUMENTS

| JP | 2005-168600 A | 6/2005 |
| JP | 2012-511965 A | 5/2012 |

(Continued)

OTHER PUBLICATIONS

"Biometrics." Merriam-Webster.com. https://www.merriam-webster.com/dictionary/biometrics (Aug. 17, 2020). (Year: 2020).*

(Continued)

*Primary Examiner* — Lindsey G Wehrheim
(74) *Attorney, Agent, or Firm* — Pearne & Gordon LLP (57) ABSTRACT

A physiological information management system includes sensors to be attached to patients to acquire physiological information of the patients and a mobile device. The mobile device includes a patient information acquiring section configured to acquire patient IDs identifying the patients, a sensor information acquiring section configured to acquire sensor IDs identifying the sensors, a controller configured to associate the patient IDs and the sensor IDs with each other, a wireless communicating section configured to receive sensor signals corresponding to the physiological information, from the sensors identified by the sensor IDs associated with the patient IDs, and a displaying section configured to display the physiological information based on the sensor signals.

10 Claims, 6 Drawing Sheets

(52) U.S. Cl.
CPC ............. *H04W 4/38* (2018.02); *A61B 5/0205* (2013.01); *A61B 2562/08* (2013.01)

(56) References Cited

U.S. PATENT DOCUMENTS

| | | | |
|---|---|---|---|
| 2005/0206518 A1* | 9/2005 | Welch ................... | G16H 40/67 340/539.12 |
| 2011/0152629 A1* | 6/2011 | Eaton .................... | G16H 40/63 600/300 |
| 2012/0108917 A1 | 5/2012 | Libbus et al. | |
| 2013/0218582 A1* | 8/2013 | LaLonde ............... | A61B 5/686 705/2 |
| 2015/0015417 A1 | 1/2015 | Libbus et al. | |
| 2015/0123810 A1 | 5/2015 | Hernandez-Rosas et al. | |
| 2015/0123811 A1 | 5/2015 | Hernandez-Rosas et al. | |
| 2015/0123812 A1 | 5/2015 | Hernandez-Rosas et al. | |
| 2015/0123813 A1 | 5/2015 | Hernandez-Rosas et al. | |
| 2016/0088372 A1 | 3/2016 | Hernandez-Rosas et al. | |
| 2016/0089066 A1 | 3/2016 | Hernandez-Rosas et al. | |
| 2016/0095148 A1 | 3/2016 | Hernandez-Rosas et al. | |
| 2017/0277962 A1 | 9/2017 | Kudo | |
| 2018/0125397 A1 | 5/2018 | Hernandez-Rosas et al. | |
| 2019/0269356 A1 | 9/2019 | Hernandez-Rosas et al. | |
| 2020/0093406 A1 | 3/2020 | Hernandez-Rosas et al. | |
| 2021/0007640 A1 | 1/2021 | Hernandez-Rosas et al. | |

FOREIGN PATENT DOCUMENTS

| | | |
|---|---|---|
| JP | 2017-503619 A | 2/2017 |
| JP | 2017-086664 A | 5/2017 |
| JP | 2017-169768 A | 9/2017 |
| JP | 2017-219934 A | 12/2017 |
| WO | 2017-040700 A2 | 3/2017 |

OTHER PUBLICATIONS

Japanese Office Action dated Oct. 5, 2021 issued in Japanese Patent Application No. 2017-249706.

* cited by examiner

MOBILE DEVICE, SENSOR, PHYSIOLOGICAL INFORMATION MANAGEMENT METHOD, AND COMPUTER READABLE MEDIUM STORING PHYSIOLOGICAL INFORMATION PROCESSING PROGRAM

CROSS-REFERENCE TO RELATED APPLICATION

The present application claims priority to Japanese Patent Application No. 2017-249706 filed on Dec. 26, 2017 the entire content of which is incorporated herein by reference.

BACKGROUND

The presently disclosed subject matter relates to: a mobile device configured to process physiological information of a patient, a sensor configured to be attached to the patient to acquire the physiological information, a physiological information management method, a physiological information processing program which causes the mobile device to execute the physiological information management method, and a computer readable medium storing the physiological information processing program.

According to a first related art, a physiological information measurement system includes a sensor and a display device (see, e.g., JP2017-086664A). The sensor is attached to a patient to acquire physiological information of the patient. The sensor is wiredly connected to the display device. The sensor transmits a signal corresponding to the acquired physiological information to the display device. The display device displays the physiological information of the patient that corresponds to the received signal.

According to a second related art, a physiological information display system includes a sensor, a wireless transmitter, and a display device (see, e.g., JP2005-168600A). The sensor is attached to a patient to acquire physiological information of the patient. The sensor is wiredly connected to the wireless transmitter. The wireless transmitter wirelessly transmits a signal corresponding to the acquired physiological information to the display device. The display device displays the physiological information of the patient that corresponds to the received signal.

To reduce weight of a device and to improve flexibility of a movement of a patient, it is desired to make a connection between a sensor and a display device completely wireless. However, a wired connection can function as means for visually checking a link between a patient to whom the sensor is attached, and the display device or a wireless transmitter.

In the configuration of the first related art, for example, the sensor and the display device are directly and wiredly connected to each other. In this case, the fact that the physiological information displayed on the display device is the information of the patient to whom the sensor is attached is clear at a glance. If the connection between the sensor and the display device is made wireless, a careful check has to be performed in advance to make sure that the patient to whom the sensor is attached and the displayed physiological information are associated with each other.

With the configuration of the second related art, the degree of freedom of movement is provided with respect to the display device. However, the patient is required to carry the wireless transmitter. If the connection between the sensor and the wireless transmitter is made wireless, a careful check becomes necessary to make sure that the sensor and the wireless transmitter are associated with the same patient.

SUMMARY

Illustrative aspects of the presently disclosed subject matter improves flexibility of a movement of a patient by making a sensor wireless and also facilitates a management of physiological information.

According an illustrative aspect of the presently disclosed subject matter, a mobile device includes a patient information acquiring section configured to acquire patient IDs identifying patients, a sensor information acquiring section configured to acquire sensor IDs identifying sensors to be attached to the patients to acquire physiological information of the patients, a controller configured to associate the patient IDs and the sensor IDs with each other, a wireless communicating section configured to receive sensor signals corresponding to the physiological information, from the sensors identified by the sensor IDs associated with the patient IDs, and a displaying section configured to display the physiological information based on the sensor signals.

According another illustrative aspect of the presently disclosed subject matter, a physiological information management method is provided. In a physiological information management system including sensors to be attached to patients to acquire physiological information of the patients and a mobile device having a processor, the method is executed by the processor. The method includes causing the mobile device to acquire patient IDs identifying the patients, causing the mobile device to identify sensor IDs identifying the sensors, causing the mobile device to associate the patient IDs and the sensor IDs with each other, causing the mobile device to receive sensor signals corresponding to the physiological information, from the sensors identified by the sensor IDs associated with the patient IDs, and displaying the physiological information on the mobile device based on the sensor signals.

According another illustrative aspect of the presently disclosed subject matter, a non-transitory computer readable medium storing a physiological information processing program which, when executed by the processor, causes the processor to execute the method described above.

DETAILED DESCRIPTION

Figure 1:
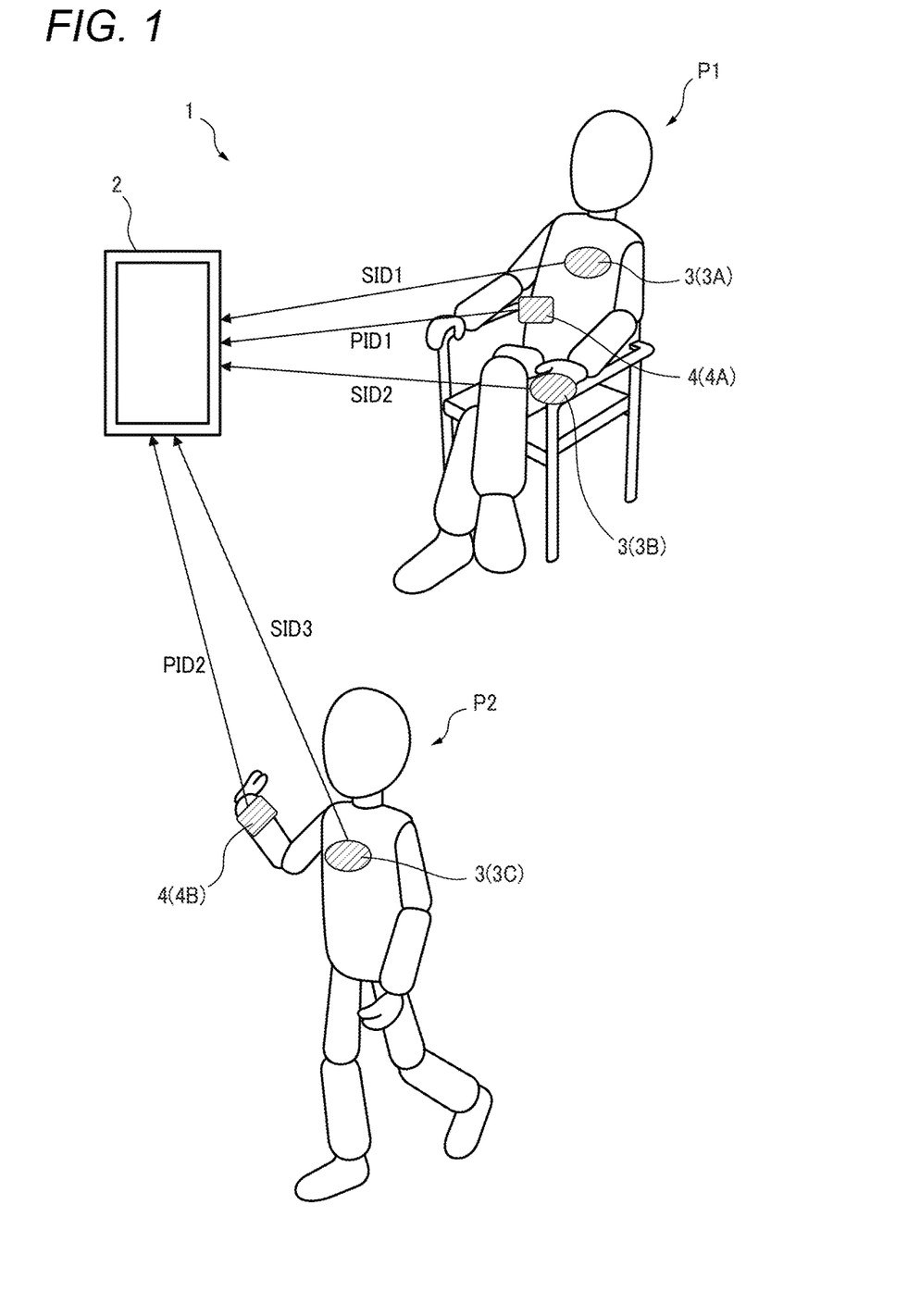
FIG. 1 illustrates an example of a configuration of a physiological information management system according to an embodiment of the presently disclosed subject matter.

Hereinafter, an embodiment will be described in detail with reference to the accompanying drawings. FIG. 1 illustrates an example of a configuration of a physiological information management system 1 according to an embodiment of the presently disclosed subject matter.

The physiological information management system 1 is configured to manage physiological information of patients. In FIG. 1, a first patient P1 and a second patient P2 are illustrated. The physiological information includes values of various physiological parameters. Examples of the physiological parameters include a body temperature, a blood pressure, an electrocardiogram, brain waves, and an arterial oxygen saturation (SpO2). The physiological information management system 1 includes a mobile device 2, sensors 3, and patient identifiers 4.

The mobile device 2 is a portable device having a displaying function and an information processing function. Examples of the mobile device 2 include a smartphone, a tablet terminal, and a head-mounted display. The configuration of the mobile device 2 will be described in detail later.

The sensors 3 are configured to be attached to a patient to acquire physiological information of the patient. Each sensor 3 includes a sensor identifier. The sensor identifier holds information that identifies the individual sensor. The information identifying the individual sensor may be provided on a package of the sensor or a body of the sensor in a form of image data such as a text or a bar code indicative of a serial number, or in a form of non-image data that are to be transmitted through non-contact communication.

In the example illustrated in FIG. 1, the sensors 3 include a first sensor 3A, a second sensor 3B, and a third sensor 3C. The first sensor 3A is attached to a chest of the first patient P1. The second sensor 3B is attached to a finger tip of the first patient P1. The third sensor 3C is attached to a chest of the second patient P2. The first sensor 3A and the third sensor 3C are, for example, electrodes configured to acquire electrocardiogram. The second sensor 3B is, for example, a probe configured to acquire arterial oxygen saturation.

Each patient identifier 4 is an article which holds information identifying the corresponding individual patient. Examples of the patient identifier 4 include a wrist band configured to be attached to an arm of the patient, a name tag configured to be attached to a cloth of the patient, and a nameplate configured to be attached to a bed or a medical ward in which the patient stays. The information identifying the individual patient may be provided in a form of image data such as a text or a bar code indicative of a name or a number of the patient, or in a form of non-image data that are to be transmitted through non-contact communication.

In the example illustrated in FIG. 1, the patient identifiers 4 include a first patient identifier 4A and a second patient identifier 4B. The first patient identifier 4A is attached to a cloth of the first patient P1 in a form of a name tag. The second patient identifier 4B is attached to the arm of the second patient P2 in a form of a wrist band.

Figure 2A:
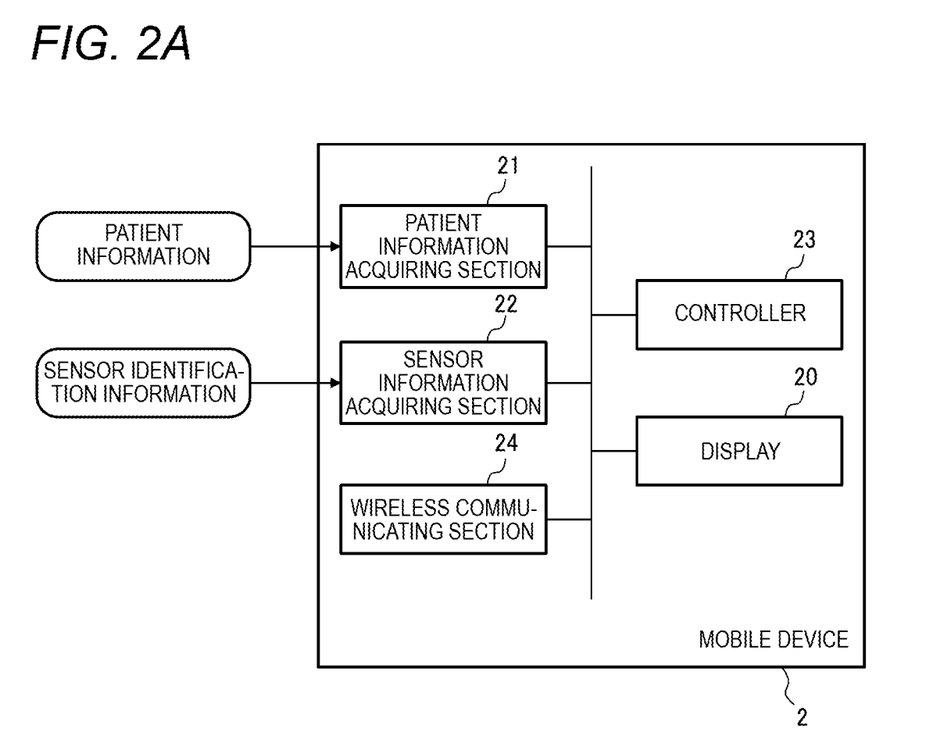
FIGS. 2A and 2B illustrate a configuration of a mobile device and a sensor of the physiological information management system.

FIG. 2A illustrates a functional configuration of the mobile device 2. The mobile device 2 includes a displaying section 20, a patient information acquiring section 21, a sensor information acquiring section 22, a controller 23, and a wireless communicating section 24. The displaying section 20, the patient information acquiring section 21, the sensor information acquiring section 22, the controller 23, and the wireless communicating section 24 are communicably connected to one another.

The displaying section 20 is configured to display various kinds of information. Examples of the displaying section 20 include a liquid crystal display device and an organic EL display device. The displaying section 20 may include a touch panel allowing a touch input.

The patient information acquiring section 21 is configured to acquire patient identification information from the patient identifiers 4. In the case where the patient identification information is provided in a form of image information such as a text or a bar code, the patient information acquiring section 21 may include a camera to acquire the image information. In the case where the patient identification information is provided in a form of non-image data, the patient information acquiring section 21 may be configured to perform wireless near field communication (NFC) or wireless Bluetooth (registered trademark) communication through which the non-image data can be acquired in a non-contact manner.

The sensor information acquiring section 22 is configured to acquire sensor identification information from the sensors 3. In the case where the sensor identification information is provided in a form of image information such as a text or a bar code, the sensor information acquiring section 22 may include a camera to acquire the image information. In the case where the sensor identification information is provided in a form of non-image data, the sensor information acquiring section 22 may be configured to perform wireless near field communication (NFC) or wireless Bluetooth (registered trademark) communication through which the non-image data can be acquired in a non-contact manner.

The controller 23 is configured to associate the patient identification information acquired by the patient information acquiring section 21 with the sensor identification information acquired by the sensor information acquiring section 22. An example of this process will be described in detail with reference to FIGS. 1 and 3.

Figure 3:
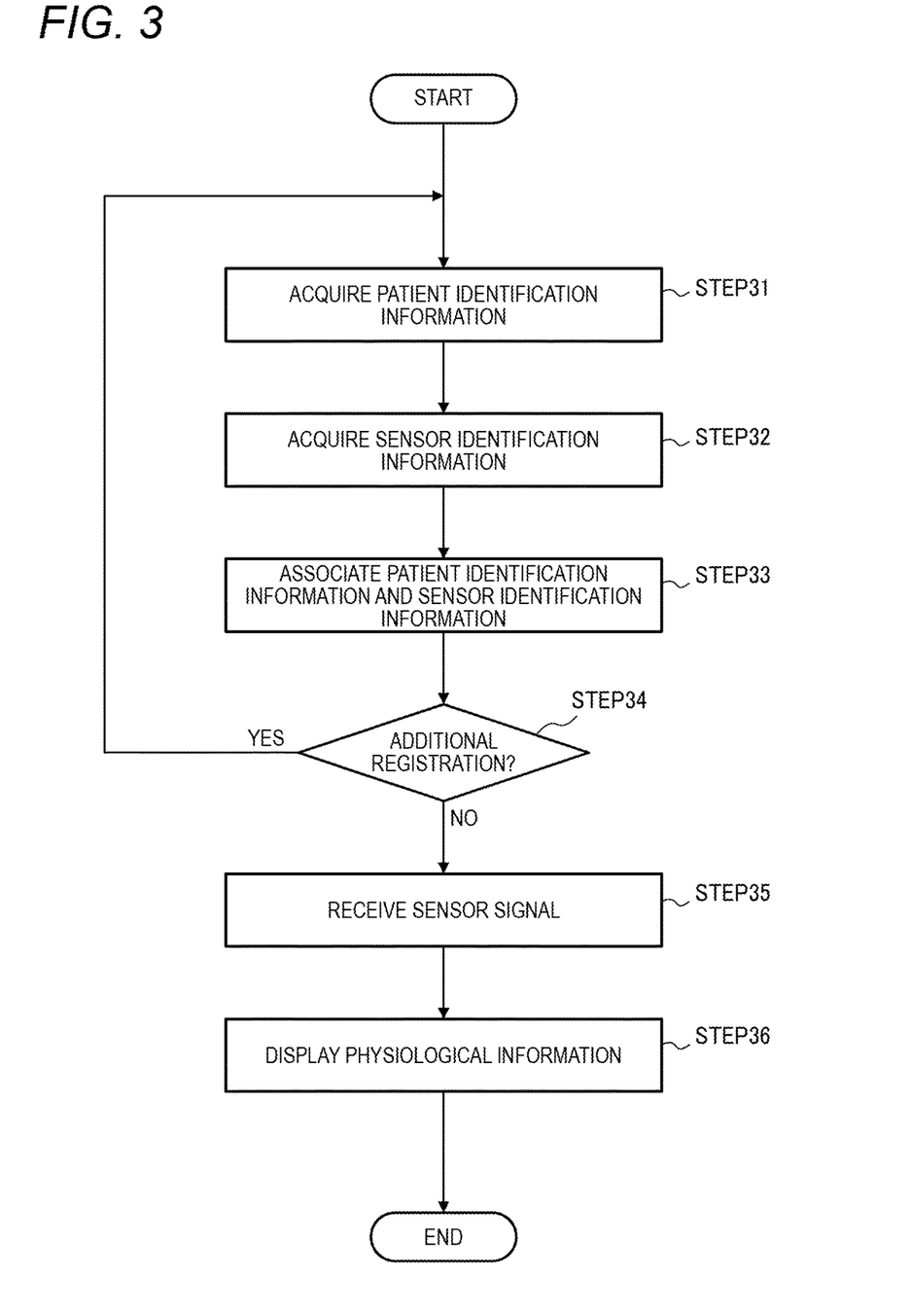
FIG. 3 illustrates a flow of a processing to be performed by the mobile device.

As illustrated in FIG. 3, first, the patient identification information is acquired by the patient information acquiring section 21 (STEP 31). For example, the controller 23 causes a message for prompting the user to acquire patient identification information, to be displayed on the displaying section 20. In the example illustrated in FIG. 1, by using the patient information acquiring section 21, the user acquires patient identification information PID1 of the first patient P1 from the first patient identifier 4A of the first patient P1.

Then, sensor identification information is acquired by the sensor information acquiring section 22 (STEP 32). For example, the controller 23 causes a message for prompting the user to acquire sensor identification information, to be displayed on the displaying section 20. In the case of the example illustrated in FIG. 1, by using the sensor information acquiring section 22, the user acquires sensor identification information SID1 of the first sensor 3A, and sensor identification information SID2 of the second sensor 3B. The first sensor 3A and the second sensor 3B are attached to the first patient P1.

When the completion of the acquisition of patient identification information, and the completion of the acquisition of sensor identification information are notified to the mobile device 2 by the user, the patient identification information and the sensor identification information are associated with each other by the controller 23 (STEP 33). The notification to the mobile device 2 may be performed by an operating one or more buttons (including those displayed on the displaying section 20) or a voice input.

In the embodiment, the controller 23 associates the patient identification information PID1 acquired from the first patient identifier 4A, with the sensor identification information SID1 acquired from the first sensor 3A, and the sensor identification information SID2 acquired from the second sensor 3B, and then stores these sets of information in a predetermined storage area. Therefore, information indicative of the first sensor 3A and the second sensor 3B being attached to the first patient P1 is stored.

Then, it is checked whether additional registration exists or not (STEP 34). For example, the controller 23 causes a message for checking whether additional registration exists or not, to be displayed on the displaying section 20. In the case of the example illustrated in FIG. 1, the second patient P2 exists.

In this case, the acquisition of patient identification information (STEP 31), the acquisition of sensor identification information (STEP 32), and the association of the patient identification information and the sensor identification information (STEP 33) are repeated. In the case of the example illustrated in FIG. 1, the patient identification information PID2 acquired from the second patient identifier 4B, and sensor identification information SID3 acquired from the third sensor 3C are associated with each other, and then stored in a predetermined storage area. Therefore, information indicative the third sensor 3C being attached to the second patient P2 is stored.

The order of the acquisition of patient identification information (STEP 31) and the acquisition of sensor identification information (STEP 32) may be reversed. However, the series of processes including the acquisitions and association of the two kinds of identification information are performed for each patient.

Then, it is checked whether additional registration exists or not (STEP 34). In the case of the example illustrated in FIG. 1, there is no patient who must be additionally registered. Therefore, the user inputs information indicating that additional registration is not necessary, in the mobile device 2 (N in STEP 34).

The wireless communicating section 24 illustrated in FIG. 2A is configured to wirelessly communicate with the sensors 3. The controller 23 is configured to request the senor 3 which is identified by the sensor identification information associated with the patient identification information, to perform communication authentication.

Figure 2B:
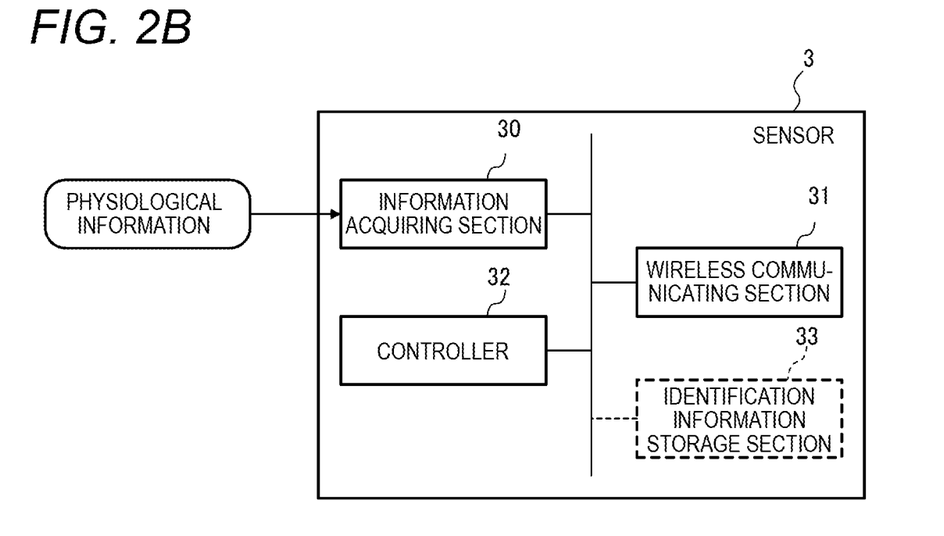

FIG. 2B illustrates a functional configuration of each sensor 3. The sensor 3 includes an information acquiring section 30, a wireless communicating section 31, and a controller 32. The information acquiring section 30, the wireless communicating section 31, and the controller 32 are communicably connected to one another.

The sensor 3 is configured to acquire physiological information of a patient through the information acquiring section 30. Namely, the information acquiring section 30 includes an adequate configuration according to physiological information of a patient which is to be acquired.

The wireless communicating section 31 is configured to wirelessly communicate with the mobile device 2.

The controller 32 is configured to cause, when the wireless communicating section 31 receives a signal requesting communication authentication, the wireless communicating section 31 to return a confirmation signal toward the mobile device 2 which has transmitted the request signal. When the confirmation signal is received by the mobile device 2, authentication of wireless communication is established between the mobile device 2 and the sensor 3.

The controller 32 is configured to cause the wireless communicating section 31 to transmit a sensor signal toward the mobile device 2 with respect to which communication authentication is established. The sensor signal is a signal corresponding to the physiological information which is acquired by the information acquiring section 30.

As illustrated in FIG. 3, the sensor signal which is transmitted from the sensor 3 is received by the mobile device 2 (STEP 35). That is, the wireless communicating section 24 of the mobile device 2 receives the sensor signal from the sensor 3 which is identified by sensor identification information associated with patient identification information. In the case of the example illustrated in FIG. 1, the wireless communicating section 24 receives the sensor signal from each of the first to third sensors 3A to 3C.

Then, the physiological information is displayed on the displaying section 20 of the mobile device 2 (STEP 36). The sensor signal which is received by the wireless communicating section 24 is visualized through adequate processes, and then displayed as the physiological information acquired by the sensor 3, on the displaying section 20. In the case of the example illustrated in FIG. 1, an electrocardiogram which is acquired by the first sensor 3A, and the arterial oxygen saturation which is acquired by the second sensor 3B are displayed as physiological information of the first patient P1, and an electrocardiogram which is acquired by the third sensor 3C is displayed as physiological information of the second patient P2.

According to the above-described configuration, only physiological information which is based on the sensor signal transmitted from the sensor(s) 3 that is identified by sensor identification information associated with patient identification information is displayed on the displaying section 20 of the mobile device 2.

In the case where the above-described association process is not performed on the second patient P2 illustrated in FIG. 1, for example, wireless communication between the mobile device 2 and the third sensor 3C is not conducted. Therefore, the physiological information of the second patient P2 which is based on the sensor signal transmitted from the third sensor 3C is not displayed on the displaying section 20 of the mobile device 2.

Figure 4:
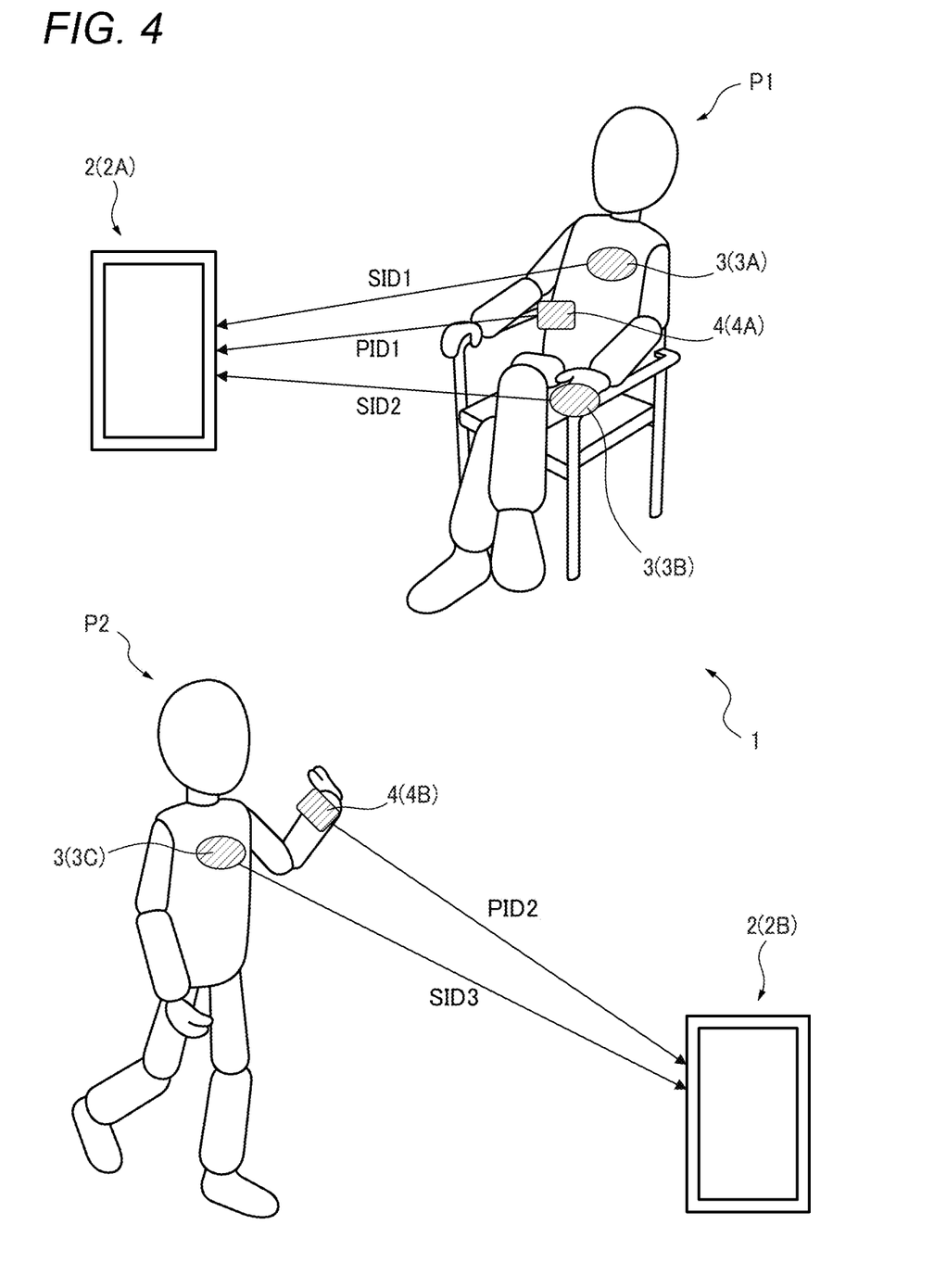
FIG. 4 illustrates another example of a configuration of the physiological information management system.

As illustrated in FIG. 4, the mobile device 2 may include a first mobile device 2A and a second mobile device 2B. In the case where a process of associating the first patient P1 with the first sensor 3A and the second sensor 3B is performed in the first mobile device 2A, and a process of associating the second patient P2 with the third sensor 3C is performed in the second mobile device 2B, physiological information relating to the first sensor 3A and the second sensor 3B is not displayed on the second mobile device 2B, and that relating to the third 3C is not displayed on the first mobile device 2A.

Even when wired connection is not provided, therefore, conviction that the physiological information displayed on the displaying section 20, and the patient to whom the sensor 3 is attached are associated with each other is easily available. Moreover, the patient is not required to carry an independent wireless transmitter for relaying a sensor signal. Therefore, the configuration where the sensors 3 are formed into wireless devices facilitates management of physiological information while improving the degree of freedom of movement of a patient.

Furthermore, it is not necessary to incorporate a memory for storing patient identification information, and a processor for executing complex processes, in each of the sensors 3. Therefore, the size and weight of the sensor 3 can be prevented from being increased, and moreover the cost of the sensor 3, which is often used disposably, can be suppressed from being raised.

Next, an example of a configuration for establishing communication authentication with the sensor 3 which is identified by a sensor identification signal associated with patient identification information will be described with reference to FIGS. 5 and 6. Here, a case where the process of associating the first patient P1 with the first sensor 3A and the second sensor 3B is performed in the first mobile device 2A, and the process of associating the second patient P2 with the third sensor 3C is performed in the second mobile device 2B will be described.

The wireless communicating section 31 of each of the sensors 3 may be configured to transmit an advertising signal. The advertising signal may contain sensor identification information identifying the individual sensor 3 which is the transmission source. As illustrated in FIG. 2B, the sensor 3 may include an identification information storage section 33. The sensor identification information contained in the advertising signal may be stored in the identification information storage section 33.

The controller 23 of the mobile device 2 may be configured to determine, when the wireless communicating section 24 receives the advertising signal, whether the sensor identified by the advertising signal coincides with that identified by the sensor identification information acquired by the sensor information acquiring section 22 or not. In other words, the controller 23 may be configured to determine whether the sensor identified by the advertising signal coincides with that identified by the sensor identification information associated with the patient identification information or not.

Figure 5:
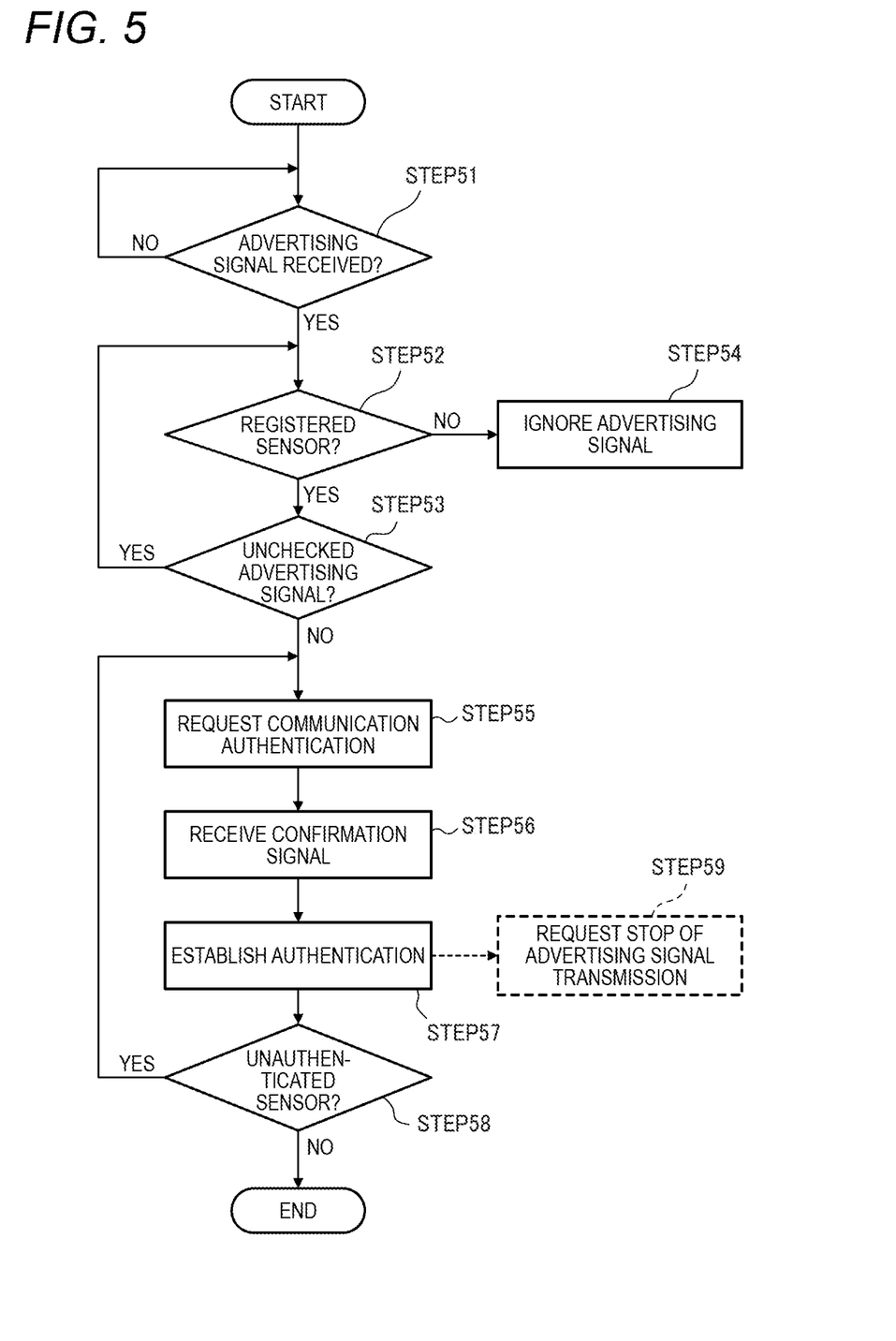
FIG. 5 illustrates a flow of a communication authentication to be performed between the mobile device and the sensor.
Figure 6A:
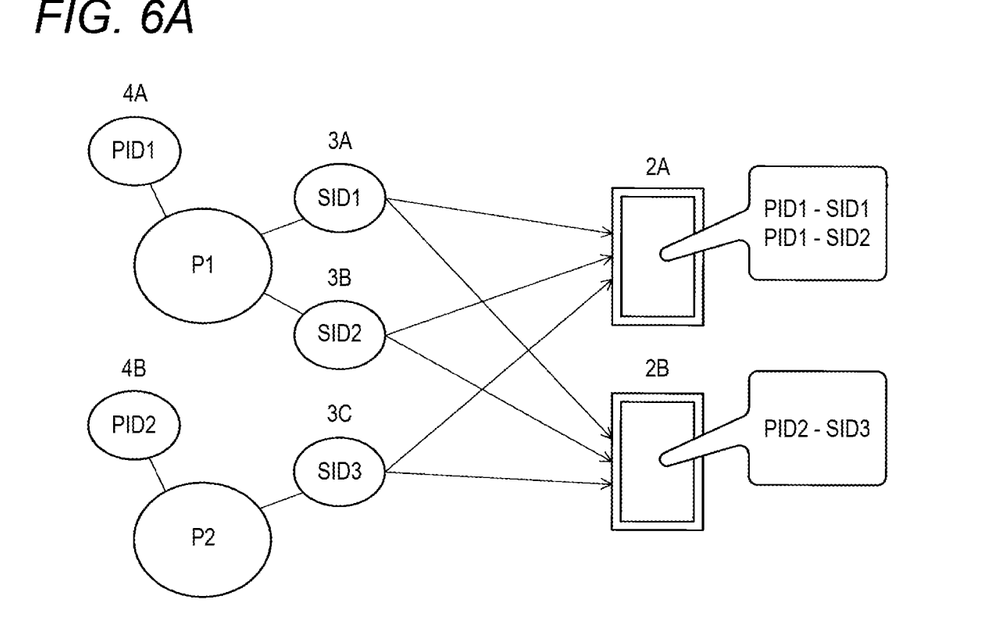
FIGS. 6A and 6B are diagrams illustrating examples of the communication authentication.
Figure 6B:
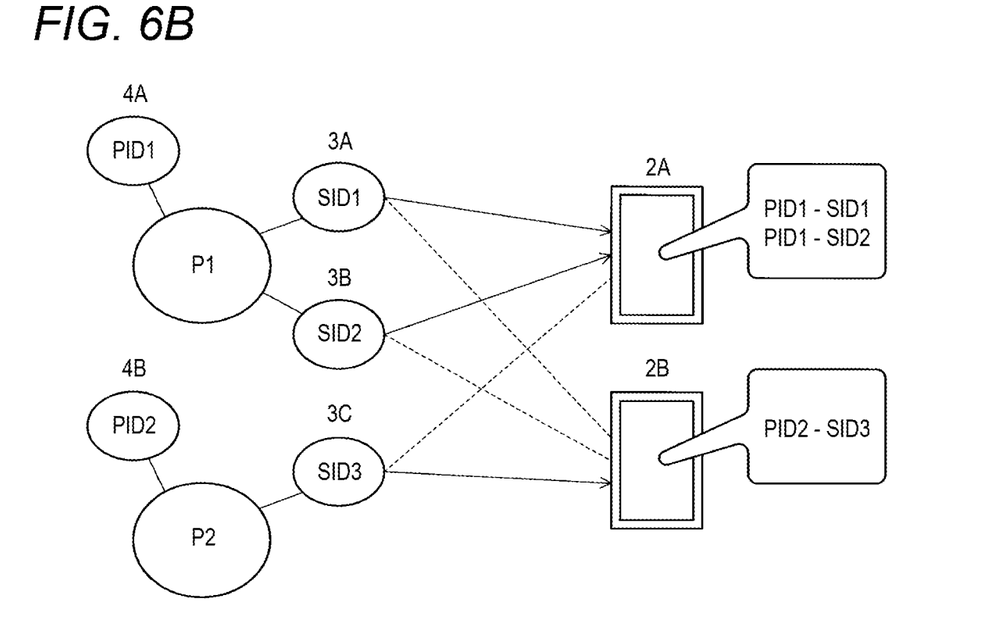

In the example illustrated in FIG. 6A, both the wireless communicating section 24 of the first mobile device 2A, and the wireless communicating section 24 of the second mobile device 2B receive advertising signals which are transmitted respectively from the first, second, and third sensors 3A, 3B, 3C (STEP 51 in FIG. 5).

In the case where the sensor 3 identified by the advertising signal is the first sensor 3A, the controller 23 of the first mobile device 2A determines whether the first sensor 3A is included in the sensors 3 which are identified by the sensor identification information associated with the patient identification information or not (STEP 52).

In the first mobile device 2A, the sensor identification information SID1 identifying the first sensor 3A is associated with the patient identification information PID1 of the first patient P1 (Y in STEP 52). Then, it is checked whether an advertising signal which is not used in the determination exists or not (STEP 53). In the example, the advertising signal transmitted from the second sensor 3B, and that transmitted from the third sensor 3C are not used in the determination (Y in STEP 53). Therefore, the process returns to STEP 52.

In the case where the sensor 3 identified by the advertising signal is the second sensor 3B, the controller 23 of the first mobile device 2A determines whether the second sensor 3B is included in the sensors 3 which are identified by the sensor identification information associated with the patient identification information or not (STEP 52).

In the first mobile device 2A, the sensor identification information SID2 identifying the second sensor 3B is associated with the patient identification information PID1 of the first patient P1 (Y in STEP 52). Then, it is checked whether an advertising signal which is not used in the determination exists or not (STEP 53). The advertising signal transmitted from the third sensor 3C has not yet been used in the determination (Y in STEP 53). Therefore, the process again returns to STEP 52.

In the case where the sensor 3 identified by the advertising signal is the third sensor 3C, the controller 23 of the first mobile device 2A determines whether the third sensor 3C is included in the sensors 3 which are identified by the sensor identification information associated with the patient identification information or not (STEP 52).

In the first mobile device 2A, the sensor identification information SID3 identifying the third sensor 3C is not associated with the patient identification information PID1 of the first patient P1 (N in STEP 52). In this case, as illustrated in FIG. 6B, the controller 23 of the first mobile device 2A ignores the advertising signal transmitted from the third sensor 3C (STEP 54).

Also in the second mobile device 2B, the same or similar process is executed. In the second mobile device 2B, as described above, the sensor identification information SID3 identifying the third sensor 3C is associated with the patient identification information PID2 of the second patient P2. As illustrated in FIG. 6B, therefore, the advertising signals which are transmitted respectively from the first and second sensors 3A, 3B are ignored, and only the third sensor 3C is treated as the target of the below-described process.

The controller 23 of each of the mobile devices 2 may be configured to request the sensor to perform communication authentication, if it is determined that the sensor identified by the advertising signal coincides with that identified by the sensor identification information.

In the example, the controller 23 of the first mobile device 2A causes the wireless communicating section 24 to transmit a signal requesting communication authentication to the first sensor 3A (STEP 55).

In each of the sensors 3, when the wireless communicating section 31 receives the signal requesting communication authentication, as described above, the controller 32 causes the wireless communicating section 31 to return the confirmation signal toward the mobile device 2 which has transmitted the request signal.

In the example, the wireless communicating section 31 of the first sensor 3A receives the authentication request signal transmitted from the first mobile device 2A, and the controller 32 of the first sensor 3A causes the wireless communicating section 31 of the first sensor 3A to return the confirmation signal to the first mobile device 2A. The wireless communicating section 24 of the first mobile device 2A receives the confirmation signal transmitted from the first sensor 3A (STEP 56). Therefore, authentication of wireless communication is established between the first mobile device 2A and the first sensor 3A (STEP 57).

Then, it is checked whether an unauthenticated sensor exists or not (STEP 58). In the example, the second sensor 3B has not yet undergone authentication (Y in STEP 58). Therefore, the process returns to STEP 55.

The controller 23 of the first mobile device 2A causes the wireless communicating section 24 to transmit a signal requesting communication authentication to the second sensor 3B (STEP 55). The wireless communicating section 31 of the second sensor 3B receives the authentication request signal transmitted from the first mobile device 2A. The controller 32 of the second sensor 3B causes the wireless communicating section 31 of the second sensor 3B to return the confirmation signal to the first mobile device 2A. The wireless communicating section 24 of the first mobile device 2A receives the confirmation signal transmitted from the second sensor 3B (STEP 56). Therefore, authentication of wireless communication is established between the first mobile device 2A and the second sensor 3B (STEP 57).

In the example, an unauthenticated sensor does not exist with respect to the first mobile device 2A (N in STEP 58). Therefore, the authentication process is ended.

Also in the second mobile device 2B, the same or similar process is executed. The controller 23 of the second mobile device 2B causes the wireless communicating section 24 to transmit a signal requesting communication authentication to the third sensor 3C (STEP 55). The wireless communicating section 31 of the third sensor 3C receives the authentication request signal transmitted from the second mobile device 2B. The controller 32 of the third sensor 3C causes the wireless communicating section 31 of the third sensor 3C to return the confirmation signal to the second mobile device 2B. The wireless communicating section 24 of the second mobile device 2B receives the confirmation signal transmitted from the third sensor 3C (STEP 56). Therefore, authentication of wireless communication is established between the second mobile device 2B and the third sensor 3C (STEP 57), and the authentication process is ended.

According to the configuration in which an advertising signal is used, the communication authentications between the mobile devices 2 and the sensors 3 are easily automatized.

The controller 23 of each of the mobile devices 2 may be configured to cause the wireless communicating section 24 to transmit a stop request signal requesting the sensor with respect to which communication authentication is established, to stop the transmission of the advertising signal.

The controller 32 of the sensor 3 may be configured to cause, when the wireless communicating section 31 receives the stop request signal from the mobile device 2, the wireless communicating section 31 to stop the transmission of the advertising signal.

As illustrated in FIG. 5 by the broken lines, namely, the controller 23 of the mobile device 2 may request the sensor with respect to which communication authentication is established, to stop the transmission of the advertising signal (STEP 59).

In the above example, the controller 23 of the first mobile device 2A causes the wireless communicating section 24 to transmit the stop request signal for stopping the transmission of the advertising signal, to each of the first and second sensors 3A, 3B. The controller 32 of each of the first and second sensors 3A, 3B causes the wireless communicating section 31 to stop the transmission of the advertising signal.

According to the configuration, in the case where there are a plurality of mobile devices 2, the burden of the communication authentication can be reduced.

When, during execution of the communication authentication with respect to the third sensor 3C in the second mobile device 2B, the first and second sensors 3A, 3B stop the transmission of the advertising signal, the first and second sensors 3A, 3B are eliminated from candidates for communication authentication. Therefore, a case sometimes occurs where a time period extending until communication authentication is established between the second mobile device 2B and the third sensor 3C can be shortened.

The stop of transmission of an advertising signal may not be always performed in response to the request issued by the mobile device 2. For example, the controller 32 of each of the sensors 3 may be configured to assume that communication with the mobile device 2 is established when the confirmation signal is returned, and to spontaneously stop transmission of an advertising signal.

The controller 23 of the mobile device 2 may be configured to start the communication authentication with respect to one or more sensors attached to another patient, after the communication authentication is established with respect to all sensors 3 attached to a certain patient. For example, a case where, with respect to the same mobile device 2, the first sensor 3A and the second sensor 3B are associated with the first patient P1, and the third sensor 3C is associated with the second patient P2 will be described.

In this case, first, the communication authentication which has been described with reference to FIG. 5 is performed on the first and second sensors 3A, 3B that are associated with the first patient P1. The transmission of a signal requesting communication authentication to the third sensor 3C that is associated with the second patient P2 is performed after communication authentication with the mobile device 2 is established with respect to both the first and second sensors 3A, 3B. The order of the first patient P1 and the second patient P2 may be reversed.

According to the configuration, while the authentication process is automatized, the risk of erroneously performing communication authentication in which the sensor 3 associated with the second patient P2 is recognized as a sensor associated with the first patient P1 can be reduced.

The transmission of the sensor signal from each of the sensors 3 to the mobile device 2 is performed through wireless communication, and therefore a case where communication is interrupted may occur depending on the communication environment. The controller 23 of the mobile device 2 may be configured to automatically recover the communication with the sensor 3, in the case where the communication with the sensor 3 with respect to which communication authentication is established is interrupted for a period shorter than a predetermined time period.

According to the configuration, it is possible to avoid performing the communication authentication each time the communication is interrupted, thereby providing a comfortable use environment to a user.

On the other hand, the controller 23 of the mobile device 2 may be configured to perform, in a case where the communication with the sensor 3 with respect to which communication authentication is established is interrupted for a period equal to or longer than the predetermined time period, perform a notification without recovering the communication with the sensor. The notification may be performed on the user by using at least one of visual notification, audible notification, and haptic notification. Examples of the notification include a display of a message, lighting of a specific light source, an output of a warning sound, and generation of vibration.

It is considered that the time period of communication interruption is made equal to or longer than the predetermined time period, by a cause such as displacement of the attachment position, dropping off, or malfunction of the sensor 3. Under such conditions, checking of the current situations ought to have preference over execution of a process of trying recovery of communication. According to the configuration, the user can be prompted to rapidly recover the wireless communication environment under an unexpected situation.

Several possible examples of the configurations of the patient information acquiring section 21 and the sensor information acquiring section 22 have been described. However, at least one of the patient information acquiring section 21 and the sensor information acquiring section 22 preferably includes a camera. That is, at least one of the patient identification information and the sensor identification information is preferably provided in a form of image information. In this case, the user takes an image of at least one of the patient identification information and the sensor identification information with the camera, thereby acquiring the information.

Usually, the mobile device 2 includes a general-purpose camera. In the configuration, at least one of the patient identification information and the sensor identification information can be easily acquired without additionally disposing a dedicated device. Moreover, acquisition of information involves visual recognition, and therefore the certainty and reliability of the work are improved.

In the mobile device 2, at least one part of the function of at least one of the patient information acquiring section 21, sensor information acquiring section 22, controller 23, and wireless communicating section 24 may be realized by cooperation of the processor and memory which are included in the mobile device 2.

Examples of the processor include a CPU, an MPU, and a GPU. The processor may have a plurality of processor cores. Examples of the memory include a ROM and a RAM. Various programs to be executed by the processor, and the like may be stored in the ROM. The RAM has a plurality of work areas in which various programs to be executed by the processor, and the like are stored. For example, the processor designates at least a part of programs stored in the ROM, develops the designated programs in the RAM, and executes various processes in cooperation with the RAM.

While the presently disclosed subject matter has been described with reference to a certain embodiment thereof for facilitating understanding of the presently disclosed subject matter, the scope of the presently disclosed subject matter n is not limited to the embodiments described above, and it will be understood by those skilled in the art that various changes and modifications may be made therein without departing from the scope as defined by the appended claims.

The numbers of the patients, mobile devices 2, and sensors 3 illustrated in FIGS. 1 and 4 are mere examples, and may be optional.

In the embodiment described above, the physiological information processing program which causes the processor of the mobile device 2 to execute the physiological information management method is stored in the memory of the mobile device 2. However, at least part of the physiological information management method may be executed by a processor of a server device provided in a network to which the mobile device 2 can be connected. In this case, at least part of the physiological information processing program which causes the processor of the mobile device 2 to execute at least part of the physiological information management method is stored in a storage section of the server device.

Physiological information to be displayed on the first mobile device 2A, and physiological information to be displayed on the second mobile device 2B may be wirelessly transmitted to a central monitor which is not illustrated. On the central monitor, physiological information of at least one patient which is managed through the first mobile device 2A, and physiological information of at least one patient which is managed through the second mobile device 2B may be collectively displayed for centralized management.

What is claimed is:

1. A mobile device including:
   a patient information acquiring section configured to acquire patient IDs identifying patients;
   a sensor information acquiring section configured to acquire sensor IDs identifying sensors for acquiring physiological information of the patients;
   a controller configured to associate the patient IDs and the sensor IDs with each other;
   a wireless communicating section configured to receive sensor signals corresponding to the physiological information, from the sensors identified by the sensor IDs associated with the patient IDs; and
   a displaying section configured to display the physiological information based on the sensor signals,
   wherein the sensor IDs are acquired from advertising signals transmitted by the sensors and received by the mobile device, and
   wherein, when the wireless communicating section receives, from at least one of the sensors, one of the advertising signals including a sensor ID identifying the at least one of the sensors, the controller:
      determines whether the at least one of sensors identified by the one of the advertising signals coincides with one of the sensors identified by one of the sensor IDs associated with a corresponding one of the patient IDs, and
      causes the wireless communicating section to transmit a signal requesting the at least one of the sensors determined to coincide with the one of the sensors, to perform a communication authentication.

2. The mobile device according to claim 1, wherein the controller causes the wireless communicating section to transmit a signal for stopping a transmission of the one of the advertising signals to the at least one of the sensors with respect to which the communication authentication is established.

3. The mobile device according to claim 1, wherein, in a case where the sensors identified by the sensor IDs includes at least one sensor attached to a first patient and at least one sensor attached to a second patient, the controller causes, after the communication authentication is established with respect to all of the at least one sensor attached to the first patient, the wireless communicating section to transmit the signal requesting the at least one sensor attached to the second patient to perform the communication authentication.

4. The mobile device according to claim 1, wherein, in a case where a communication with the at least one of the sensors with respect to which communication authentication is established is interrupted for a period shorter than a predetermined time period, the controller automatically recovers the communication with the at least one of the sensors.

5. The mobile device according to claim 4, wherein, in a case where the communication with the at least one of the sensors with respect to which communication authentication is established is interrupted for a period equal to or longer than the predetermined time period, the controller performs a notification without recovering the communication with the at least one of the sensors.

6. The mobile device according to claim 1, wherein at least one of the patient IDs and the sensor IDs contains image information, and
   wherein at least one of the patient information acquiring section and the sensor information acquiring section includes a camera to acquire the image information.

7. A sensor comprising:
   an information acquiring section configured to acquire physiological information of a patient;
   a wireless communicating section configured to transmit an advertising signal containing a sensor ID identifying the sensor; and
   a controller configured to cause, when the wireless communicating section receives a request for communication authentication from a mobile device, the wireless communicating section to transmit a confirmation signal to the mobile device to establish the communication authentication, and to cause, after the communication authentication is established, the wireless communicating section to transmit a sensor signal corresponding to the physiological information.

8. The sensor according to claim 7, wherein, after the confirmation signal is transmitted, the controller causes the wireless communicating section to stop the transmission of the advertising signal.

9. A physiological information management method which, in a physiological information management system including sensors for acquiring physiological information of the patients and a mobile device having a processor, is executed by the processor, the method comprising:
   causing the mobile device to acquire patient IDs identifying the patients;
   causing the mobile device to identify sensor IDs identifying the sensors from advertising signals transmitted by the sensors and received by the mobile device;
   causing the mobile device to associate the patient IDs and the sensor IDs with each other;
   causing the mobile device to receive sensor signals corresponding to the physiological information, from the sensors identified by the sensor IDs associated with the patient IDs; and
   displaying the physiological information on the mobile device based on the sensor signals.

10. A non-transitory computer readable medium storing a physiological information processing program which, when executed by the processor, causes the processor to execute the method of claim 9.

* * * * *